United States Patent [19]

Klein et al.

[11] Patent Number: 4,495,067
[45] Date of Patent: Jan. 22, 1985

[54] APPARATUS FOR PREPARATION OF INFUSION GRADE WATER

[75] Inventors: Elias Klein, New Orleans, La.; Douglas J. Beach, Burlington, N.C.

[73] Assignee: Tracor, Inc., Austin, Tex.

[21] Appl. No.: 428,436

[22] Filed: Sep. 29, 1982

Related U.S. Application Data

[63] Continuation of Ser. No. 212,142, Dec. 2, 1980, abandoned.

[51] Int. Cl.$^3$ ............................................. B01D 31/00
[52] U.S. Cl. .................................. 210;87; 210/257.2; 210/259; 210/433.2
[58] Field of Search ................ 210/90, 87, 927, 500.2, 210/321.1, 433.2, 259, 636, 257.2, 258

[56] References Cited

U.S. PATENT DOCUMENTS

| | | | |
|---|---|---|---|
| 2,702,034 | 2/1955 | Walter | 128/214 |
| 3,187,750 | 6/1965 | Tenczar, Jr. | 128/272 |
| 3,774,763 | 11/1973 | Yall et al. | 210/321.1 X |
| 3,836,458 | 9/1974 | Wallis et al. | 210/23 |
| 3,945,380 | 3/1976 | Dabney et al. | 128/214 |
| 3,955,833 | 5/1976 | Silbert | 285/3 |
| 3,986,506 | 10/1976 | Garber et al. | 128/214 |
| 4,072,610 | 2/1978 | Gow et al. | 210/90 |
| 4,261,834 | 4/1981 | deWinter | 210/500.2 X |
| 4,265,760 | 5/1981 | Abel et al. | 210/927 X |

OTHER PUBLICATIONS

Culligan Brochure, "Aqua–Summa", Reagent Grade Water System, 2/80, 4 pp.
Gelman newsletter, Spring, 1980, "Basic Design Features for a High Purity System, 4 pp.
Gelman Brochure, "How, Pure, Pure, Water", 4 pp.
Nelsen, "Removal of Pyrogens from Parenteral Solutions by Ultrafiltration", from Pharmaceutical Technology, 5/1978, pp. 46–48,44 and 80.
United States Pharmacopoeia XIX, pp. 613, 592, 593, 539 and 540.
Technical Report 7612, U.S. Army Bioengineering R&D Lab., Fort Detrick, Md., 11/1976.
Sweadner et al., "Filtration Removal . . . States of Aggregation", from Applied and Env. Microbiology, Oct. 1977, pp. 382–385.

*Primary Examiner*—Frank Spear
*Attorney, Agent, or Firm*—Arnold, White & Durkee

[57] ABSTRACT

An apparatus is disclosed for the preparation of infusion grade water for use in the preparation of parenteral solutions. The apparatus is comprised of a two component system including a chemical purification unit and an endotoxin filter receiving assembly. Chemical purification of the water is achieved by treating the feed water [any potable water source] using a sequence of carbon adsorption, reverse osmosis, deionization, and membrane filtration. The chemically pure water from this system is used as a feed water to a low molecular weight cutoff membrane ultrafilter, which is an integral part of a presterilized manifold with receiving bags. The receiving bags may contain premeasured solutes in sterile nonpyrogenic powder form or in concentrated solution form to yield by dilution typical parenteral solutions ready for administration.

2 Claims, 2 Drawing Figures

APPARATUS FOR PREPARATION OF INFUSION GRADE WATER

BACKGROUND OF THE INVENTION

This is a continuation of application Ser. No. 212,142, filed Dec. 2, 1980, now abandoned.

The invention relates to a portable system for preparing infusion grade water.

It is known that in the preparation of parenteral solutions, the starting water must be of a high purity. Parenteral solutions must be prepared without either chemical or biological contaminants.

The basic requirements for infusion grade solutions are that they be bacteria free, have a base of chemically pure water, are endotoxin free and monitored in a strict quality control system. The main concern in parenteral solutions is the presence of pyrogens. A pyrogen is defined as any chemical or biological substance that will cause a rise in temperature, that is, a febrile response when intravenously or intramuscularly introduced into a subject mammal. It has been found that endotoxins of gram-negative bacteria are pyrogenic and are the most common cause of septic shock.

Bacterial endotoxins are lipopolysaccharides derived from the cell wall of the gram-negative bacteria. They are polymeric materials having molecular weights between 400,000 and 4,000,000 Daltons. The polymer can be depolymerized to basic units of 10,000 to 20,000 Daltons by being treated with strong detergents or bile salts. However, in pure water depolymerization would not occur.

Pyrogenic reactions to endotoxins can be regularly elicited in man, rabbits and certain other mammals. In minimal dosages endotoxin will induce an elevation from the normal temperature of the recipient. Acute endotoxin poisoning can lead to irreversible shock and death.

Endotoxin is shed from the outer surface of gram-negative bacteria. It is destroyed by a heat treatment of 175° C. for a period of approximately two hours. Endotoxin is not affected by sterilization via autoclaving.

The most widely used method for pyrogen removal is distillation. In this method large quantities of water are distilled, stored and then packaged in a sterile environment for delivery to hospitals and emergency units. Various chemical treatments have also been proposed to remove pyrogens from water and parenteral preparations. The main difficulty in the chemical treatment lies in the removal of the chemical and its reaction products after the completion of the treatment process.

Removal of endotoxin by any means other than distillation was not practical prior to the development of ultrafiltration membranes. Ultrafilters allow selection in a dissolved species. Since endotoxins of the gram-negative bacteria have a high molecular weight ultrafilters may be used to remove these pyrogenic endotoxins.

While being the most effective historical method for producing pyrogen free water, distillation is in terms of resources the most costly system available. Further, distillation systems do not lend themselves to practical utility in military field hospitals and other emergency field medical units. Military medical units require large volumes of sterile, nonpyrogenic fluids for infusion. Distillation techniques do not lend themselves to on site production on an as needed basis. Using the distillation methods requires that large inventories of sterile nonpyrogenic water be transported to the location.

With quality control and maintained sterility being a primary factor in the overall preparation and storage of sterile nonpyrogenic infusion grade water, endotoxin testing is also a constraint with regard to on-site units. Historically, a rabbit test was used to determine the presence of pyrogenic endotoxins. The rabbit test for pyrogens requires injection of 10 ml of test solution into the ear veins of three rabbits weighing not less than 1.5 kg each. The rabbits must be individually caged in a shock-free environment, and their temperature must be taken 40 minutes prior to injection and for three hours after injection. If no one rabbit shows a temperature rise of 0.6° C. or more, and if the collective increases in temperature totals no more than 1.4.° C., the test solution is determined to be nonpyrogenic. The disadvantages of the rabbit test include maintenance of the test animals, a minimum of three hours for performance, the requirement of three rabbits per test, and, the requirement of skilled personnel to administer and record the temperature changes.

With the advent of a simpler in vitro test that requires only a one hour incubation time and uses less than 1 ml of test solution the potential for qualifying field unit devices for preparation of infusion grade water increased. The test is an enzymatic reaction that occurs when certain clottable proteins found in circulating amebocytes encounter endotoxin. This test uses a Limulus Amebocyte Lysate and is referred to as LAL. Because LAL is a reliable, sensitive, and rapid in vitro test that can be performed with a minimum of equipment, a minimum space requirement and no unusual skills or personnel, it is a primary choice for use in an on-site field system for generation of infusion grade water.

A major problem in practical generation of infusion grade water on-site lies in retaining the nonpyrogenic characteristic of the water. In conjunction with this lies the problem of rapid access to the nonpyrogenic solution for quality control within the output assembly without risking introduction of endotoxins.

SUMMARY OF THE INVENTION

The present invention provides a portable water treatment apparatus for preparation of sterile, nonpyrogenic water using ultrafiltration technology. The apparatus is capable of supplying water for preparation of parenteral solutions for military field hospitals and other emergency field units. The apparatus includes a system for generating chemically pure water in combination with an endotoxin filter output assembly, wherein the endotoxin filter and storage assembly are integral with respect to one another and sealed for prevention of entrance of endotoxins into the storage areas.

In accordance with the present invention a first major component of this apparatus includes a chemical purification unit for generating chemically pure water. The chemical purification unit includes a means for receiving feed water into the device, where the feed water may be potable water. The feed water is delivered to a first filter for removal of gross particulate material and other organic impurities. This first filter has an input port for receiving the potable water and an output port for discharging filtered water.

A plurality of reverse osmosis purification modules are provided in the chemical purification unit, plumbed in parallel and fluidly connected with said first filter. The reverse osmosis purification modules generate permeate water and have a retentate port for delivery of rejected water to a drain or recirculation system. The purpose of the modules is removal of inorganic and organic solutes.

A mixed bed deionizer is fluidly connected to the output of the reverse osmosis purification modules for removing residual electrolytes on the part per million level, to an acceptable predetermined concentration within the purification unit.

Finally, a means for microporous filtration is provided at the output of the deionizer to retain dislodged resin beads that may have decomposed from the mixed bed deionizer. The chemically pure water is then delivered to an endotoxin filter receiving assembly.

The receiving assembly includes an endotoxin filter of the retentive membrane ultrafilter type. The endotoxin filter removes lipopolysaccharides of gram-negative bacteria resulting in the generation of nonpyrogenic infusion grade water from the chemically pure water.

The receiving assembly further includes a receiving and storage system integrally sealed to the endotoxin membrane filter. The storage and receiving assembly includes a series of sterile bags sealed to the membrane filter by way of a sterile nonpyrogenic manifold system. Entrance to the collection bags is only through the endotoxin retentive membrane filter. The manifold is airtight with the endotoxin filter. Thus, sterile, nonpyrogenic solutions are prepared using only chemically pure water.

In a preferred embodiment of the apparatus for preparation of infusion grade water the filtration of gross particles and adsorption of organic impurities is accomplished through a carbon adsorption filter. The carbon adsorption filter may be a disposable carbon pack having an affinity for free chlorine, chloramines and other organics including chlorinated hydrocarbons.

The reverse osmosis (RO) purification is carried out by way of a plurality of desalination membrane cartridges (or hollow-fibers) plumbed in parallel and connected to the carbon adsorption filter. Each of the membrane cartridges has a retentate port for delivering rejected water to a drain or recirculation system. The RO units may be spiral wound modules or hollow fiber units preferably capable of resisting attack by chlorine, and operable in pH ranges between 3 and 11.

The preferred embodiment also includes a fines filter having a five micron cutoff connected to the carbon adsorption filter, for protecting the device from fine particulate material emanating from the carbon filter. A means for pumping, preferably a rotary or reciprocating pump may also be connected to the carbon output filter for enhancing water movement in the apparatus. A 0.22 micron electronic grade membrane filter is provided in the chemical purification unit for microporous filtering of the deionized permeate water. The deionization is accomplished in the preferred embodiment by a mixed bed deionization chamber.

The endotoxin retentive membrane filter in the preferred embodiment is a polyacrylonitrile hollow-fiber hemofilter. It will be understood to those skilled in the art that any ultrafilter having a suitable pore size for removing pyrogenic endotoxins is contemplated.

The present invention overcomes the constraints inherent in using distillation and provides a portable unit for generating nonpyrogenic water capable of use in the preparation of parenteral solutions. The present invention further contemplates a method for preparing infusion grade water including the steps of chemically purifying potable feed water and retentive ultrafiltering of the chemically pure water for removal of pyrogen causing endotoxins for use in preparation of parenteral solutions. The method includes the steps of adsorbing gross particulates and other organic impurities from potable water and then performing reverse osmosis purification for generation of permeate water by removing organic as well as inorganic impurities, to be further deionized in an effort to remove essentially all electrolytes. Finally, the water is microporously filtered to remove any resin beads dislodged from the deionizer. The chemically pure water generated by this method is then retentively ultrafiltered for removal of pyrogenic endotoxins from the water. The water is then received and stored in a manner sealable and integral with the ultrafilter.

The method further contemplates the monitoring of the conductivity of the chemically pure water as well as selectively accessing the nonpyrogenic infusion grade water for determining the presence of endotoxins.

BRIEF DESCRIPTION OF THE DRAWINGS

Other advantages and features of the present invention will become apparent from the following detailed description when taken in conjunction with the drawings in which.

DETAILED DESCRIPTION

The present invention provides an apparatus for preparation of infusion grade water. This infusion grade water may be used in preparation of parenteral solutions. In the preparation of parenteral solutions, the starting water must be of a high chemical purity and free of bacteria and pyrogens. The apparatus of the present invention meets these criteria in a two component system. The first component of the system is a chemical purification unit. Chemical purity is achieved by treating the feed water, i.e. any potable water source, using a sequence of carbon adsorption, reverse osmosis, deionization, and membrane filtration.

The chemically pure water from this unit is used to feed a low-molecular-weight cut-off membrane ultrafilter which is an integral part of a presterilized nonpyrogenic manifold with receiving bags. The receiving bags may contain premeasured solutes in sterile nonpyrogenic powder form or concentrated solution form such as electrolytes, carbohydrates, and drugs so that dilution by the nonpyrogenic water will yield typical parenteral solutions ready for administration. As a means of quality assurance, the water purification unit monitors the product water conductivity. If the product water does not conform to a predetermined conductivity level, an alarm system and bypass circuit allows for automatic shutoff.

Figure 1:
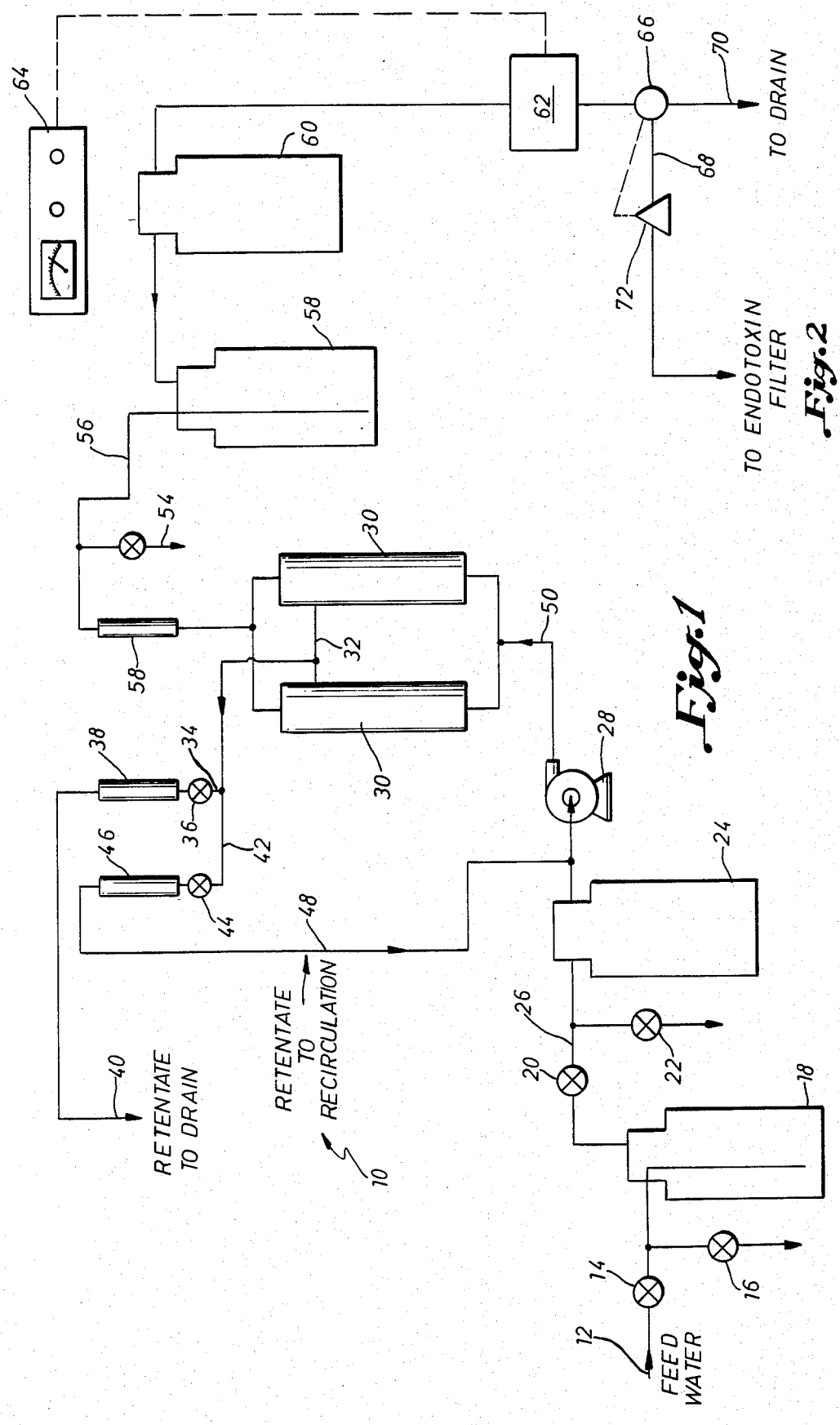
FIG. 1 is a block diagram of a chemical water purification unit in accordance with the present invention.

Referring now to the drawings and in particular to FIG. 1 where a chemical purification unit 10 in accordance with the present invention is illustrated. In the chemical purification unit 10, feed water is delivered into the system by way of an inlet port 12. This feed water may be monitored by a valve 14 and sampled at a valve port 16.

The feed water may be any potable water, for example from a garden hose. The feed water is first filtered in a carbon adsorption filter 18. This carbon adsorption filter 18 may be a disposable carbon pack. The carbon in this filter 18 is specifically designed to have a high affinity for free chlorine and chloramines as well as a wide variety of organics including chlorinated hydrocarbons. Chloramines have been clearly implicated in hemolytic episodes during hemodialysis and its absence is necessary for any water source to be used for parenteral solution use.

The purification unit 10 is provided with a valve 20 for regulating the flow of the filtered water and a valve sample port 22 for sampling the carbon filtered water.

Since carbon is particularly prone to bacterial contamination because of its porosity and affinity for organics, a disposable filter element may be used so that such bacterial contamination can be avoided by replacement of the filter after each use.

Following the carbon filter unit 18, is a "fines" filter 24. The fines filter 24 may be a 5 micron depth filter used to protect the system from fine particulates which may be released from the carbon in the carbon filter 18. The fine filter 24 is fluidly connected to the carbon filter 18 by way of conduit 26.

Further provided in the chemical purification unit 10 is a pumping apparatus for enhancing the movement of the water throughout the system. The pumping apparatus 28 may be a rotary or reciprocating pump or equivalent having a capacity of 70 gallons per hour and delivering water at 200 psi or greater.

The pressurized water is delivered to a plurality of reverse osmosis purification modules or cartridges 30. The RO modules 30 in the preferred embodiment are plumbed in parallel. Each module may be a Film Tech type FT-30 spiral wound module with each module having 6 square feet of surface area located in a housing. The FT-30 modules use a membrane that resists attack by chlorine and can be operated at a wide range of pH values on the order of 3 to 11. The retentate stream 42 emanating from the output port 32 of each of the reverse osmosis modules 30 is split. The first leg 34 is provided to deliver some rejected water through a valve 36 and rotameter 38 to a retentate drain 40. The second leg of the retentate stream 42 is provided with a valve 44 and rotameter 46 for recirculating the remainder of the rejected water through conduit 48 and back to the input of the reverse osmosis module 50. Valve 36 and 44 may be of the needle valve type and operate in conjunction with the rotameters for adjusting the flow rates of each stream while maintaining constant feed line pressure at 200 psi. This allows a variable water recovery so that the unit can be operated at high recovery when the source water is in short supply or low recovery (higher rejection) if the source water is high in salt content.

Permeate flow rate from the RO modules 30 is measured by a third rotameter 52. A valve sample port 54 is provided to monitor the reverse osmosis purification rejection.

Besides removal of large molecule organic impurities the RO modules remove inorganic impurities such as residual electrolytes. This removal assists the deionization unit in removal of electrolytes.

The permeate water is then delivered through a fluid conduit 56 to be treated by a mixed bed deionization chamber 58. The mixed bed deionizer 58 removes the residual electrolyte in the permeate water to acceptable concentrations at a level of parts per million.

The deionized permeate solution is then delivered to a microporous 5 micron filter 60 for removal of ion exchange resin fines.

In the preferred embodiment, the rotary or reciprocating pump is a Procon products, V-band clamp mount pump, model CO-1500. The reverse osmosis purification units are FT-30 Film-Tech units manufactured by Film-Tech Corporation, Minnetonka, Minn.; and the deionizer is of the type manufactured by Cole-Parmer, Chicago, Ill.

Figure 2:
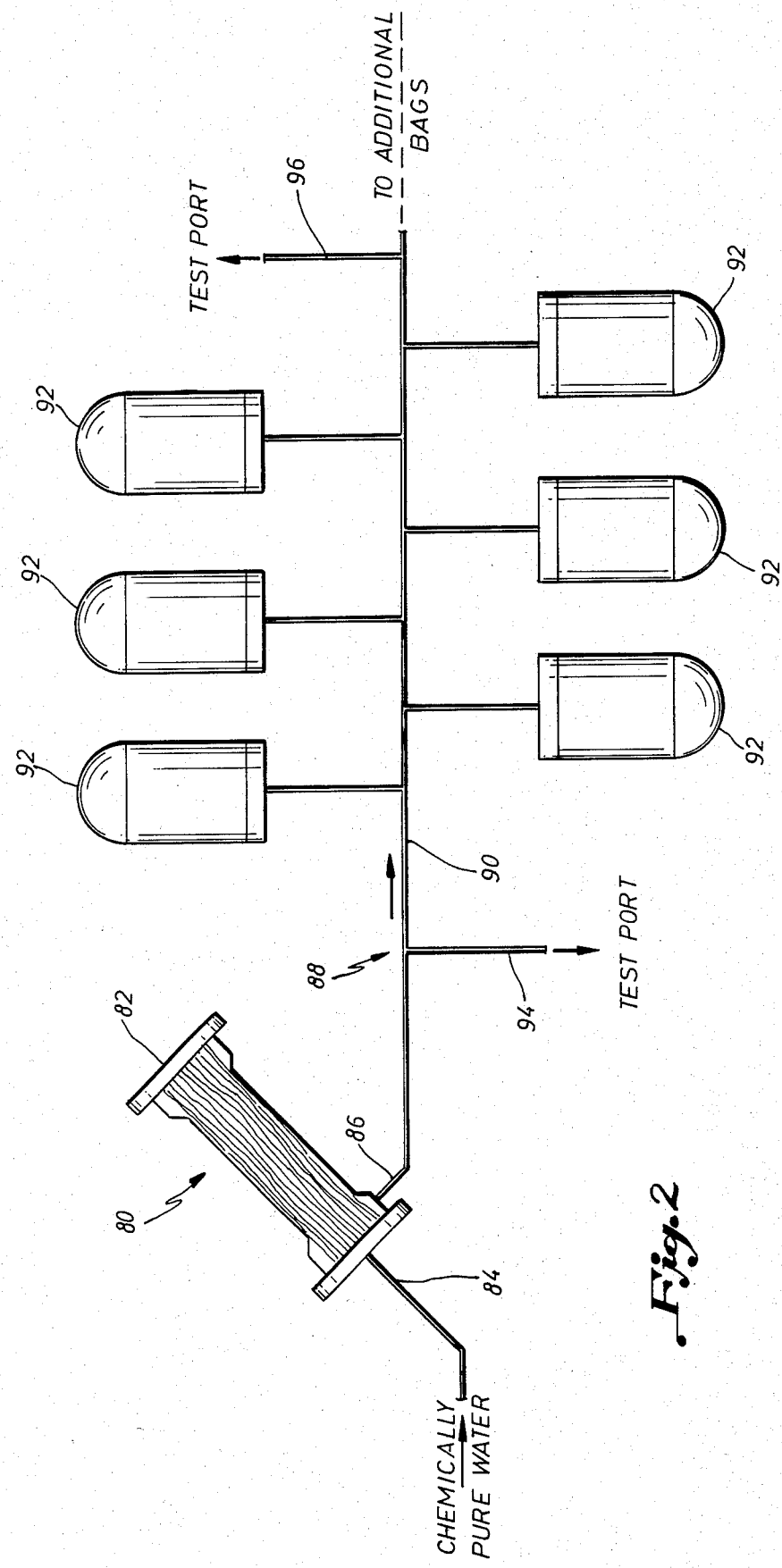
FIG. 2 is a block diagram of an endotoxin filter output assembly in accordance with the present invention.

The water delivered from the microporous filter 60 is chemically pure and ultimately delivered to an endotoxin filter output assembly as shown in FIG. 2. Prior to delivery of the chemically pure water to the endotoxin filter assembly, its conductivity is determined. Conductivity of the water product is monitored continuously by a 0.01 $CM^{-1}$ temperature compensated conductivity cell 62, electrically connected to a 0 to 20 megohm-cm resistivity monitor 64. The conductivity monitor 64 may be of the type made by Balsbaugh, model 920M. The monitor 64 provides circuitry for alarm and control valves. The alarm of monitor 64 may be set to sound if the water quality fails to meet a predetermined standard. An electronic three-way valve 66 is provided in the product line and controlled by the resistivity monitor 64. When actuated, the three-way valve 66 diverts the water from the collection assembly line 68 to a drain 70. A pressure sensitive switch 72 is also provided in the collection assembly line to protect the endotoxin filter shown in FIG. 2 from excessive pressure.

The apparatus for preparation of infusion grade water includes the chemical purification unit 10 as described above in conjunction with an endotoxin filter assembly 80 as shown in the drawing of FIG. 2. In the filter assembly 80, a bacterial and endotoxin retentive membrane filter 82 is provided. The filter 82 receives at its input port 84 chemically pure water from the chemical purification unit 10 shown in FIG. 1 and described above. The chemically pure water passes over the membranes making up the endotoxin filter 82. The endotoxin filter used in the preferred embodiment is made by Asahi Medical Company Ltd. It is a polyacrylonitrile hollow-fiber hemofilter. The filter has a 1.4 $m^2$ surface area and is presterilized by ethylene oxide. The solute molecular weight cutoff of this filter is estimated at 10–15,000 Daltons. The lipopolysachrides derived from the cell wall of negative bacteria are polymeric materials having aggregate molecular weights between 400,000 and 4,000,000 Daltons. Thus, the low molecular weight endotoxin filter 82 utilized in the endotoxin assembly 80 will trap lipopolysachrides and retain them within the filter itself.

The filtrate delivered from the output 86 of the filter 82 is delivered to a presterilized nonpyrogenic manifold and receiving bag assembly 88. The assembly 88 is integrally sealed with the filter 82.. The manifold 90 may be fabricated from 3/16"I.D. medical grade Tygon tubing and sterilizable plastic, for example polypropylene tees (not shown). A plurality of receiving bags 92 such as blood bags for example are connected to the manifold 90 via the polypropylene tees. Typically, 6 to 8 bags are used on each manifold assembly although a greater number may be utilized.

The membrane filter 82 is sealed to the sterile bags 92 via the manifold system 90. Entrance to the collection bags 92 can only be through the retentive membrane filter 82. Thus, sterile, nonpyrogen solutions can be prepared using the chemically pure water generated by the chemical purification unit 10.

An additional tee 94 may be placed at the head of the manifold 90 for sampling the filtrate from the filter 82 for presence of endotoxins. This tee would contain a sterile septum and cap.

As shown in FIG. 2, additional bags may be placed along the manifold assembly 90 with additional endotoxin test sample ports such as port 96.

Operationally, the apparatus of the present invention for preparation of infusion grade water for use in preparation of parenteral solutions includes the preparation of a chemically pure water in conjunction with a retentive ultrafiltration process. The preparation of the chemically pure water in the preferred embodiment assumes obtaining potable water and performing a sequence of carbon adsorption, reverse osmosis purification, deionization and microporous filtration to obtain a chemically pure solution.

In the preferred embodiment, retentive ultrafiltration of the chemically pure water is achieved through a filter having a low molecular weight cutoff membrane. The filtrate from the ultrafiltration step is delivered into receiving bags by way of a presterilized nonpyrogenic manifold integrally sealed to the low molecular weight filter.

An additional step in the preparation of infusion grade water involves the sampling of the filtrate from the ultrafiltration process and testing for the presence of endotoxins. This testing may be performed by either the historical rabbit test method, or the in vitro limulus amebocyte lysate (LAL) test. This quality control measure is used to validate sterility and guarantee quality of the product.

The infusion grade water may be utilized in the preparation of parenteral solutions. In the process of preparing parenteral solutions using the apparatus of the present invention, the receiving bags 92 illustrated in FIG. 2 may contain premeasured solutes in sterile nonpyrogenic powder or concentrated solution form, such as electrolytes, carbohydrates, or drugs. Dilution by nonpyrogenic water will then yield typical intravenous solutions ready for administration.

While the present invention has been described and illustrated with respect to a preferred embodiment, it will be understood to those skilled in the art that various modifications and changes such as the substitution of crosses for tees in the manifold, are contemplated to be within the spirit and scope of the invention as set forth in the appended claims.

We claim:

1. A portable apparatus for preparing infusion grade water for use in generating parenteral solutions comprising:
   a chemical purification assembly for generating chemically pure water including:
      inlet means for receiving potable feed water,
      a carbon adsorption filter for initial purification of said feed water, removing gross particulate and organic impurities, said carbon filter having an input port connected to said inlet port, and an output port for discharging filtered water,
      means for pumping said filtered water, connected to said carbon adsorption filter output port, for enhancing water movement,
      a plurality of reverse osmosis purification modules connected in parallel and connected to said carbon adsorption filter for generating permeate water,
      a mixed bed deionizer for removing residual electrolytes from said permeate water, connected to said plurality of reverse osmosis purification modules, and,
      an electronic grade membrane filter connected to said mixed bed deionizer for further filtering of said permeate deionized water resulting in an output of said chemically pure water; and,
   an endotoxin filter receiving assembly including:
      an endotoxin filter having an inlet port for receiving said chemically pure water, said endotoxin filter comprising a retentive membrane ultrafilter for removing lipopolysaccharides of gram-negative bacteria from said chemically pure water resulting in nonpyrogenic infusion grade water, and
      means for receiving and storing free of contamination said nonpyrogenic water, said collection means constructed and arranged for preparation of solutions for direct patient infusion, said means integrally sealed with said retentive membrane filter.

2. A portable device for preparation of infusion grade water comprising:
   a chemical purification assembly including:
      an inlet port for receiving feed water,
      a first filter for filtration of gross particles and organic impurities, said filter having an input port connected to said inlet port, and an output port for discharging filtered water,
      means for reverse osmosis purification of said filtered water, said means having a retentate port for delivery of rejected water, said means generating permeate water, and wherein said means for reverse osmosis purification comprises membrane cartridges plumbed in parallel, connected to said first filter, each of said cartridges having a permeate port and a retentate port for delivering said water,
      means for deionization of said permeate water connected to said means for reverse osmosis purification, and,
      a second filter connected to said means for deionization, for fine particle filtration resulting in chemically pure water;
   an endotoxin filter receiving assembly including;
      an endotoxin filter having a means for receiving said chemically pure water, said endotoxin filter removing lipopolysaccharides of gram-negative bacteria from said chemically pure water and having a means for delivery of nonpyrogenic infusion grade water, and
      collection means integrally sealed with said endotoxin filter for receiving and storing free of contamination said infusion grade water, said collection means constructed and arranged for preparation of solutions for direct patient infusion; and,
   further including a recirculation system including a valve and conduit for delivering the retentate back to the means for reverse osmosis purification, said recirculation means including a needle valve in a rotameter for adjustment of the flow rate through each of the membrane cartridges.

* * * * *

UNITED STATES PATENT AND TRADEMARK OFFICE
CERTIFICATE OF CORRECTION

PATENT NO. : 4,495,067

DATED : January 22, 1985

INVENTOR(S) : Klein et al.

It is certified that error appears in the above-identified patent and that said Letters Patent is hereby corrected as shown below:

```
Column 1, line 67 delete "on site" and insert --on-site--
Column 2, line 23 underline in vitro
Column 2, line 31 underline in vitro
Column 7, line 33 underline in vitro
```

Signed and Sealed this

Twenty-eighth Day of January 1986

[SEAL]

Attest:

DONALD J. QUIGG

Attesting Officer

Commissioner of Patents and Trademarks